US011116270B2

(12) United States Patent
Zhavoronkov et al.

(10) Patent No.: US 11,116,270 B2
(45) Date of Patent: Sep. 14, 2021

(54) ELECTRICAL CONNECTION FOR SUSPENSION BAND ATTACHMENT SLOT OF A HARD HAT

(71) Applicant: Guardhat, Inc, Detroit, MI (US)

(72) Inventors: Mikhail Zhavoronkov, Northville, MI (US); Senni Perumal, Southfield, MI (US); Saikat Dey, Birmingham, MI (US)

(73) Assignee: Guardhat, Inc., Detroit, MI (US)

(*) Notice: Subject to any disclaimer, the term of this patent is extended or adjusted under 35 U.S.C. 154(b) by 169 days.

(21) Appl. No.: 16/502,127

(22) Filed: Jul. 3, 2019

(65) Prior Publication Data
US 2019/0380417 A1 Dec. 19, 2019

Related U.S. Application Data

(60) Division of application No. 15/150,384, filed on May 9, 2016, now Pat. No. 10,383,384, which is a
(Continued)

(51) Int. Cl.
| A42B 3/04 | (2006.01) |
| A42B 3/14 | (2006.01) |
| A61B 5/02 | (2006.01) |
| A61B 5/0205 | (2006.01) |
| A61B 5/024 | (2006.01) |
| A61B 5/0245 | (2006.01) |
| A42B 3/32 | (2006.01) |

(Continued)

(52) U.S. Cl.
CPC ............. *A42B 3/04* (2013.01); *A42B 3/042* (2013.01); *A42B 3/046* (2013.01); *A42B 3/0406* (2013.01); *A42B 3/0433* (2013.01); *A42B 3/0446* (2013.01); *A42B 3/0453* (2013.01); *A42B 3/14* (2013.01); *A42B 3/147* (2013.01); *A42B 3/324* (2013.01); *A61B 5/02* (2013.01); *A61B 5/024* (2013.01); *A61B 5/0245* (2013.01); *A61B 5/02055* (2013.01); *G08B 21/02* (2013.01); *G08B 21/0446* (2013.01); *G08B 25/10* (2013.01); *H04Q 9/00* (2013.01)

(58) Field of Classification Search
CPC .......... A42B 3/0433; A42B 3/04; A42B 3/14; A42B 3/32; A42B 3/147; A42B 3/24; A42B 3/0406; A42B 3/042
USPC ..................................... 2/421, 416
See application file for complete search history.

(56) References Cited

U.S. PATENT DOCUMENTS 4,703,879 A * 11/1987 Kastendieck ........... A61F 9/027
2/422
4,719,462 A * 1/1988 Hawkins ............. A42B 3/0433
342/20

(Continued)

*Primary Examiner* — Gloria M Hale
(74) *Attorney, Agent, or Firm* — Simonelli IP, PLLC

(57) ABSTRACT

A suspension band assembly to be used to support a hard hat on a head of a user. The suspension band assembly includes a primary support loop to receive the head of the user therein. An electronic peripheral is fixedly secured to the primary support loop. An attachment strap extends out from the primary support loop to a strap distal end. An anchor is fixedly secured to the strap distal end for securing the attachment strap to the hard hat. An electrical anchor contact is fixedly secured to the anchor to provide an electrical connection between the hard hat and the electronic peripheral located on the primary support loop.

6 Claims, 9 Drawing Sheets

Related U.S. Application Data continuation-in-part of application No. 14/883,157, filed on Oct. 14, 2015, now Pat. No. 9,538,801, which is a division of application No. 14/590,596, filed on Jan. 6, 2015, now Pat. No. 9,177,458, which is a division of application No. 14/517,385, filed on Oct. 17, 2014, now Pat. No. 9,013,297.

(51) Int. Cl.
*G08B 21/04* (2006.01)
*G08B 25/10* (2006.01)
*G08B 21/02* (2006.01)
*H04Q 9/00* (2006.01)

(56) References Cited

U.S. PATENT DOCUMENTS

| | | | | |
|---|---|---|---|---|
| 4,833,726 A * | 5/1989 | Shinoda | ............ | A42B 3/30 381/376 |
| 5,404,577 A * | 4/1995 | Zuckerman | ............ | A42B 3/30 455/351 |
| 5,666,700 A * | 9/1997 | Anscher | ............ | A42B 3/08 2/421 |
| 5,678,205 A * | 10/1997 | Gray | ............ | A42B 3/10 455/348 |
| 5,685,020 A * | 11/1997 | Powell | ............ | A42B 3/08 2/421 |
| 5,845,341 A * | 12/1998 | Barthold | ............ | A42B 3/04 2/424 |
| 6,298,249 B1 * | 10/2001 | Locarno | ............ | A42B 3/14 2/417 |
| 6,862,747 B2 * | 3/2005 | Oleson | ............ | A42B 3/14 2/416 |
| 6,992,580 B2 * | 1/2006 | Kotzin | ............ | G08B 21/0453 340/539.11 |
| 7,188,767 B2 * | 3/2007 | Penuela | ............ | G01D 1/18 235/439 |
| 7,213,271 B1 * | 5/2007 | Bielefeld | ............ | A42B 3/14 2/181 |
| 7,246,385 B2 * | 7/2007 | Dennis | ............ | A42B 3/08 2/421 |
| 7,298,258 B1 * | 11/2007 | Hudgens | ............ | G08B 21/22 340/539.13 |
| 7,570,170 B2 * | 8/2009 | Wallner | ............ | A42B 3/0433 2/417 |
| 8,040,292 B2 * | 10/2011 | Ronzani | ............ | G02B 27/0176 345/8 |
| 9,013,297 B1 * | 4/2015 | Dey | ............ | A42B 3/046 340/539.11 |
| 9,177,458 B1 * | 11/2015 | Dey | ............ | A42B 3/046 |
| 9,446,273 B2 * | 9/2016 | Jang | ............ | A62D 3/36 |
| 9,538,801 B2 * | 1/2017 | Dey | ............ | G08B 25/10 |
| 9,686,136 B1 * | 6/2017 | Dey | ............ | H04W 4/70 |
| 10,383,384 B2 * | 8/2019 | Zhavoronkov | ............ | A42B 3/042 |
| 2002/0008625 A1 * | 1/2002 | Adams | ............ | G08B 21/0294 340/573.1 |
| 2003/0214408 A1 * | 11/2003 | Grajales | ............ | G08B 21/02 340/573.1 |
| 2005/0001728 A1 * | 1/2005 | Appelt | ............ | G08B 21/182 340/573.1 |
| 2005/0180129 A1 * | 8/2005 | Harris | ............ | A42B 3/0406 362/105 |
| 2009/0126059 A1 * | 5/2009 | Tack | ............ | A42B 3/04 2/2.5 |
| 2009/0251332 A1 * | 10/2009 | Senogles | ............ | H04Q 9/00 340/870.02 |
| 2011/0025492 A1 * | 2/2011 | Bravo | ............ | H04Q 9/00 340/539.11 |
| 2012/0188083 A1 * | 7/2012 | Miller, II | ............ | A61B 5/6898 340/573.1 |
| 2012/0313776 A1 * | 12/2012 | Utter, II | ............ | G16H 20/60 340/539.12 |
| 2013/0144175 A1 * | 6/2013 | Lambert | ............ | G08B 1/08 600/485 |
| 2013/0283507 A1 * | 10/2013 | Baty | ............ | A42B 3/064 2/416 |
| 2014/0000013 A1 * | 1/2014 | Redpath | ............ | H05K 1/028 2/422 |
| 2014/0109301 A1 * | 4/2014 | Hall | ............ | A42B 3/142 2/416 |
| 2014/0189938 A1 * | 7/2014 | Redpath | ............ | A42B 3/0406 2/422 |
| 2014/0197965 A1 * | 7/2014 | Park | ............ | G08B 5/22 340/870.09 |
| 2014/0208487 A1 * | 7/2014 | Orientale | ............ | A42B 3/0433 2/422 |
| 2014/0228649 A1 * | 8/2014 | Rayner | ............ | G16H 20/30 600/301 |
| 2014/0240120 A1 * | 8/2014 | Mao | ............ | G08B 25/10 340/539.11 |
| 2014/0361881 A1 * | 12/2014 | Reilly | ............ | A42B 3/046 340/407.1 |
| 2015/0059066 A1 * | 3/2015 | Ketterer | ............ | A42B 3/14 2/418 |
| 2016/0249700 A1 * | 9/2016 | Zhavoronkov | ............ | A42B 3/042 2/421 |
| 2017/0000417 A1 * | 1/2017 | Zhavoronkov | ............ | A42B 3/046 |
| 2019/0037954 A1 * | 2/2019 | Friedman | ............ | A42B 3/04 |
| 2019/0380417 A1 * | 12/2019 | Zhavoronkov | ............ | A42B 3/0406 |

* cited by examiner

US 11,116,270 B2

ELECTRICAL CONNECTION FOR SUSPENSION BAND ATTACHMENT SLOT OF A HARD HAT

This is a divisional of U.S. Pat. No. 10,383,384, which is a continuation-in-part of U.S. Pat. No. 9,538,801, which is a divisional of U.S. Pat. No. 9,177,458, which is a divisional of U.S. Pat. No. 9,013,297, which was filed on Oct. 17, 2014.

BACKGROUND ART

1. Field of the Invention

The invention relates generally to the field of 'smart' safety gear. More particularly, the invention relates to a suspension system for 'smart' safety helmet providing user with physical protection as well as enabling data and power interchange between a suspension and a hard hat.

2. Description of the Related Art

Helmets are often required when working in areas where there is a potential for injury to the head from hazards such as impact from a falling objects, scraping or bumping one's head on equipment, or contact with electrical conductors. Traditional suspension bands inside the helmet are used for spreading the helmet's weight and the force of any impact over the top of a user's head. However, as personal protective equipment becomes 'smart', suspension bands may be used for placement of various sensors and communication devices. Advantage of placing devices such as heart rate or body temperature sensors on the suspension band is that it allows direct contact user's skin. As electrical circuitry is placed on the suspension band, there is a need for a connection mechanism that would provide not only means of mechanical attachment but also electrical connectivity with main circuitry attached to the hard hat's shell.

SUMMARY OF THE INVENTION

A suspension band assembly to be used to support a hard hat on a head of a user. The suspension band assembly includes a primary support loop to receive the head of the user therein. An electronic peripheral is secured to the primary support loop. An anchor is fixedly secured to the strap distal end for securing the primary support loop to the hard hat. An electrical anchor contact is fixedly secured to the anchor to provide an electrical connection between the hard hat and the electronic peripheral located on the primary support loop.

BRIEF DESCRIPTION OF THE DRAWINGS

Advantages of the invention will be readily appreciated as the same becomes better understood by reference to the following detailed description when considered in connection with the accompanying drawings, wherein.

DETAILED DESCRIPTION OF THE PREFERRED EMBODIMENT

Figure 1:
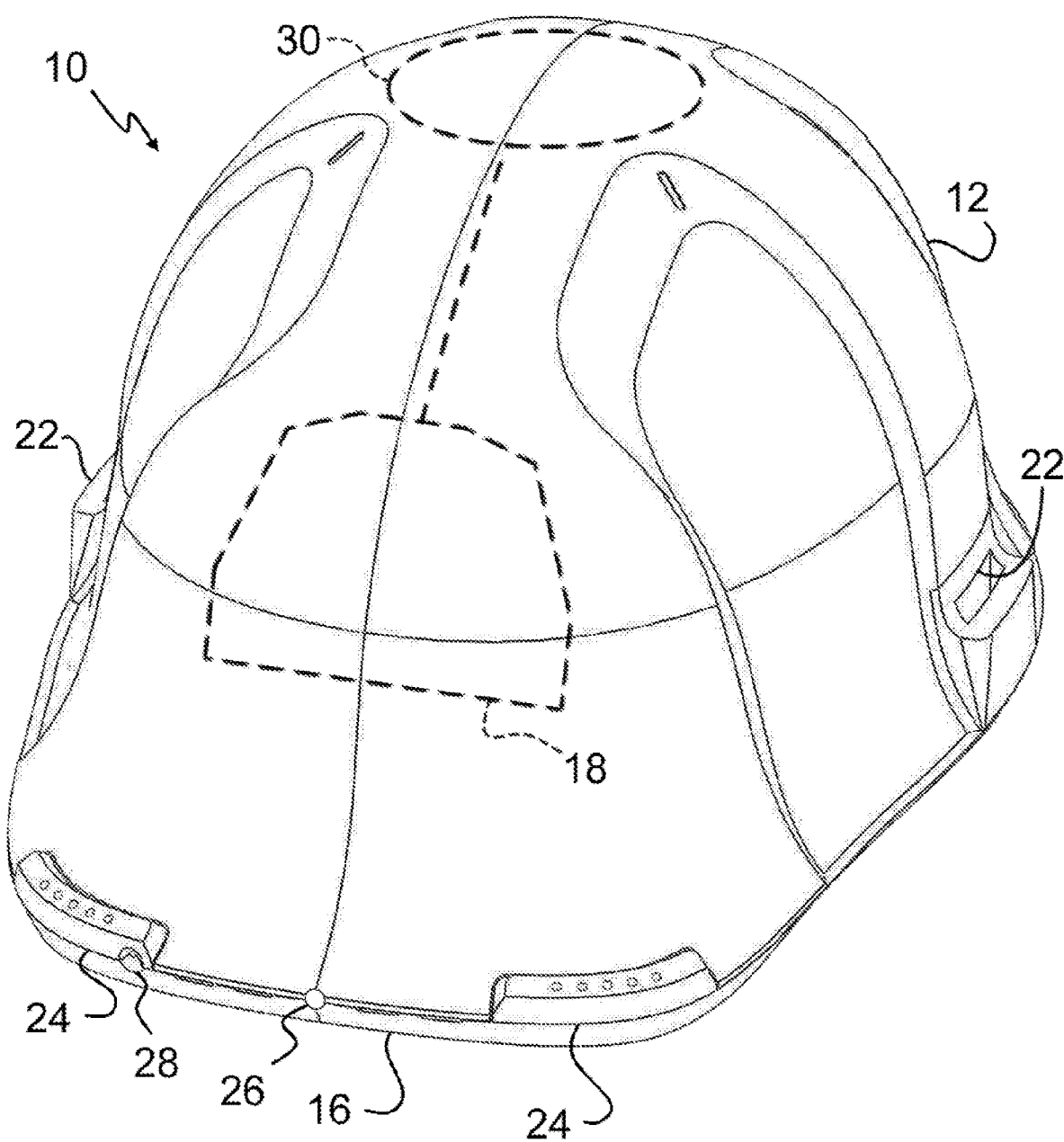
FIG. 1 is a perspective view of hard hat with electronics incorporated into the design.

Referring to FIG. 1, a smart device is generally shown at 10. While the smart device 10 is shown to be a hard hat, it should be appreciated by those skilled in the art that the smart device 10 may be any device that has a level of connectivity and computational capability.

The hard hat 10 has a hard outer shell 12 designed to cover and protect a head of the person wearing the hard hat 10. The hard hat 10 defines an opening 14 (best seen in FIG. 3) to receive the head therein. A brim 16 extends out and away from the outer shell 12 over the portion of the hard hat 10 designed to be over the face of the person wearing it.

The hard hat 10 includes a control unit 18. The control unit 18 is secured to or within the outer shell 12 and includes electronics to receive and transmit signals and memory to store signals and/or data received by devices, including but not limited to a camera 26. While a camera 26 is show at or near the brim 16, it should be appreciated by those skilled in the art that there may be fewer or more devices 26 secured to, either permanently or temporarily attached, the hard hat 10. By way of example, ear muffs with speakers may be secured to the hard hat 10 using connection ports 22. The connection ports 22 are described in greater detail in a United States patent application having Ser. No. 15/087,972, the disclosure of which is hereby incorporated by reference.

Two handle grips 24 are also located at or near the brim 16. In the embodiment shown, the brim includes the camera 26 and a light unit 28. The light unit 28 may illuminate the path in front of the user or it may be used to assist the camera 26 in recording information. The camera 26, the light 28, and all other devices that may be incorporated into or on the hard hat 10 are electrically connected to the control unit 18.

Also electrically connected to the control unit 18 is a communications unit 30. The communications unit 30 includes one or more antennae that transmit and receive signals to and from locations remote of the hard hat 10. One or more electronic communication protocols may be employed by the communications unit 30 depending on the needs of the person wearing the hard hat 10 and the functionality incorporated into the overall electronics of the hard hat 10.

Figure 2:
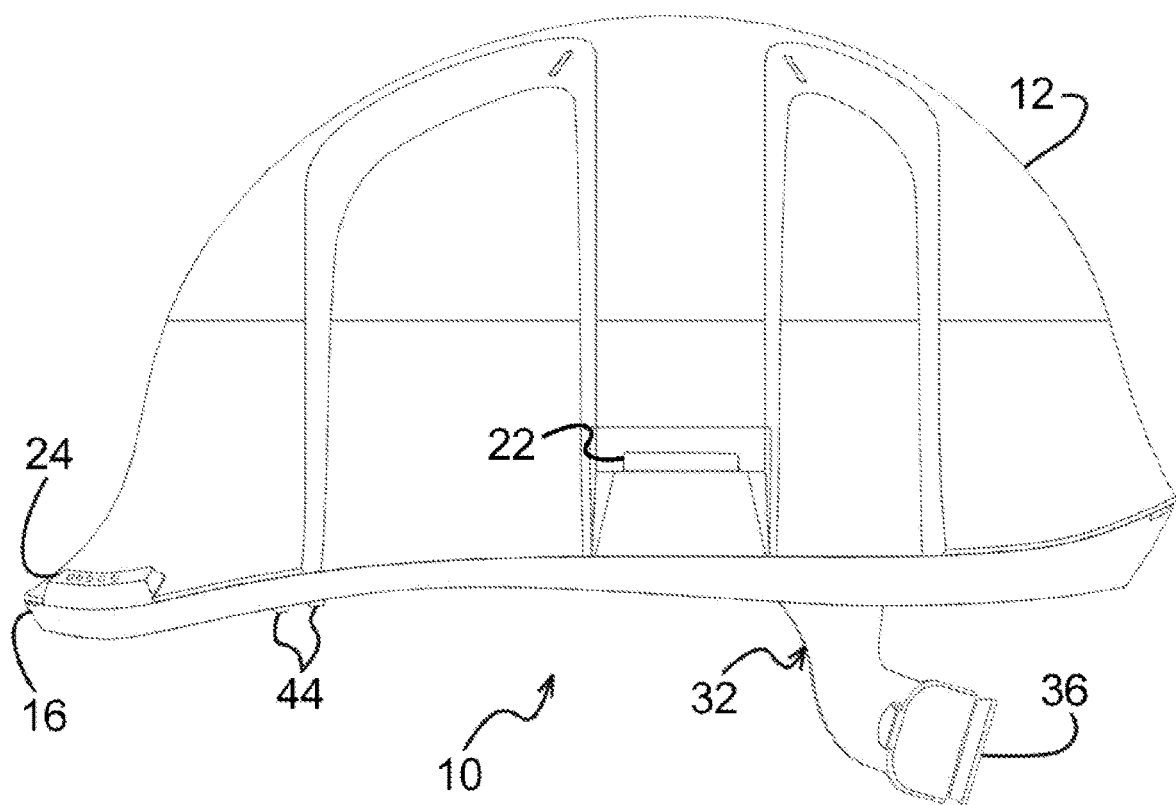
FIG. 2 is a side view of the hard hat of FIG. 1 with a suspension band.
Figure 3:
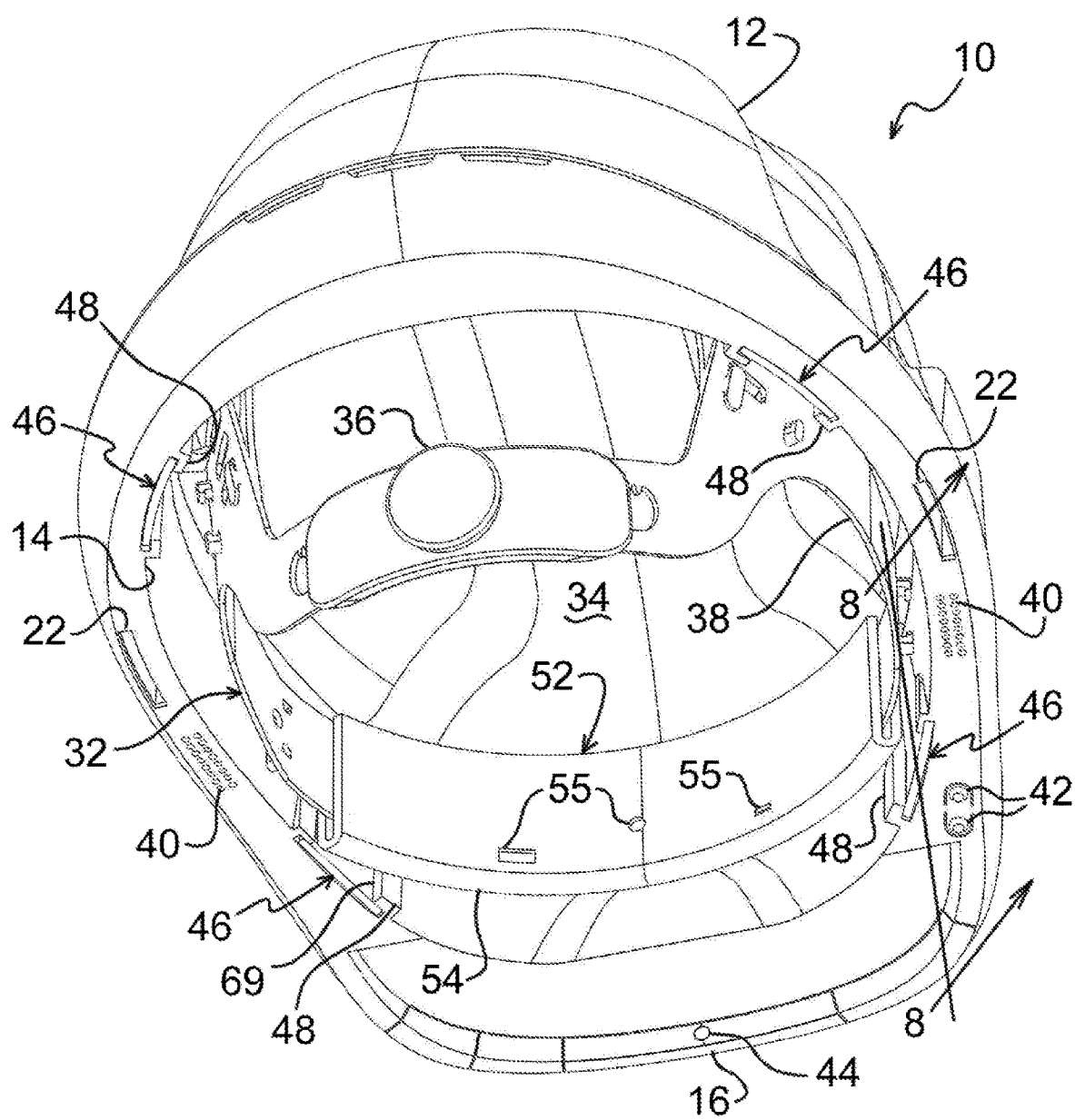
FIG. 3 is a bottom view of hard hat and suspension band of FIG. 2.
Figure 4:
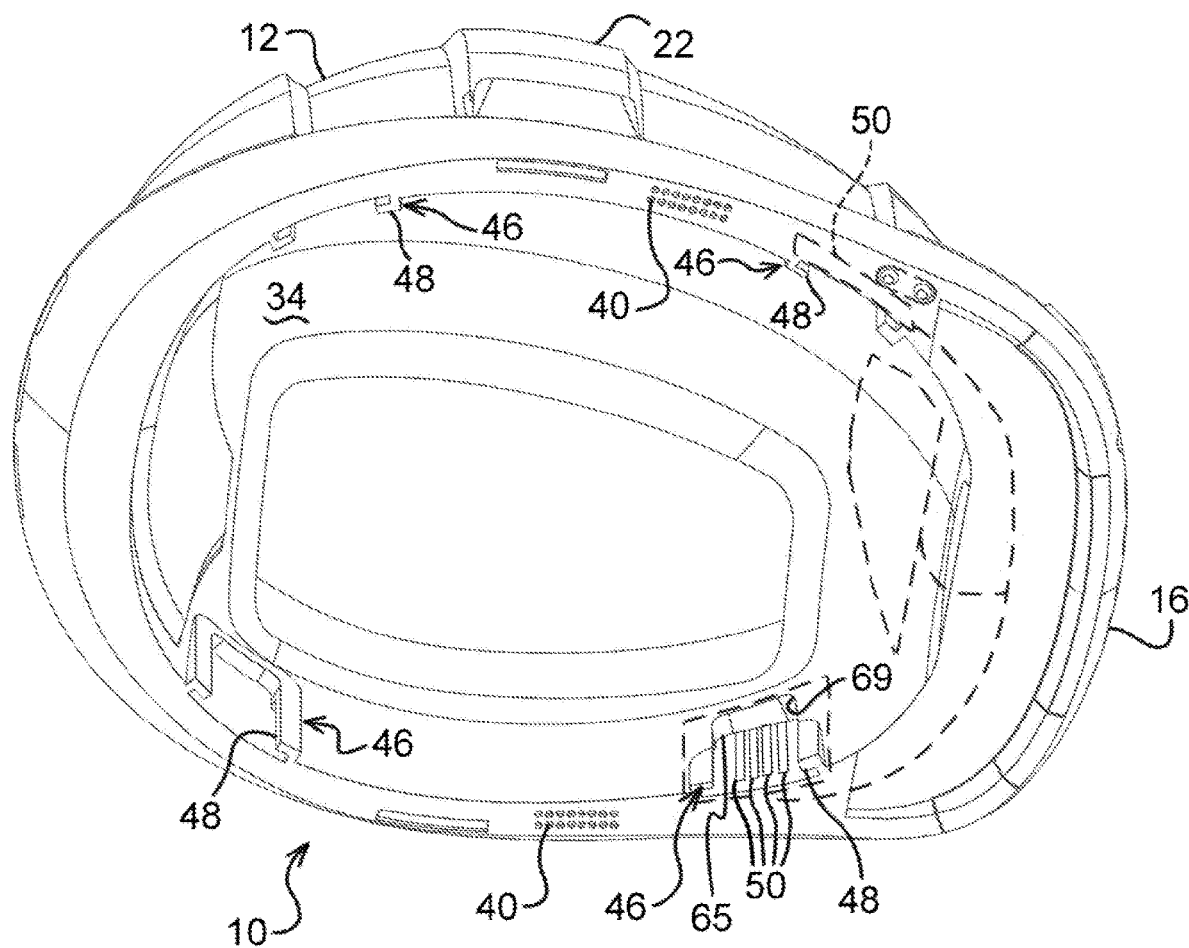
FIG. 4 is a bottom view of hard hat of FIG. 1.
Figure 5:
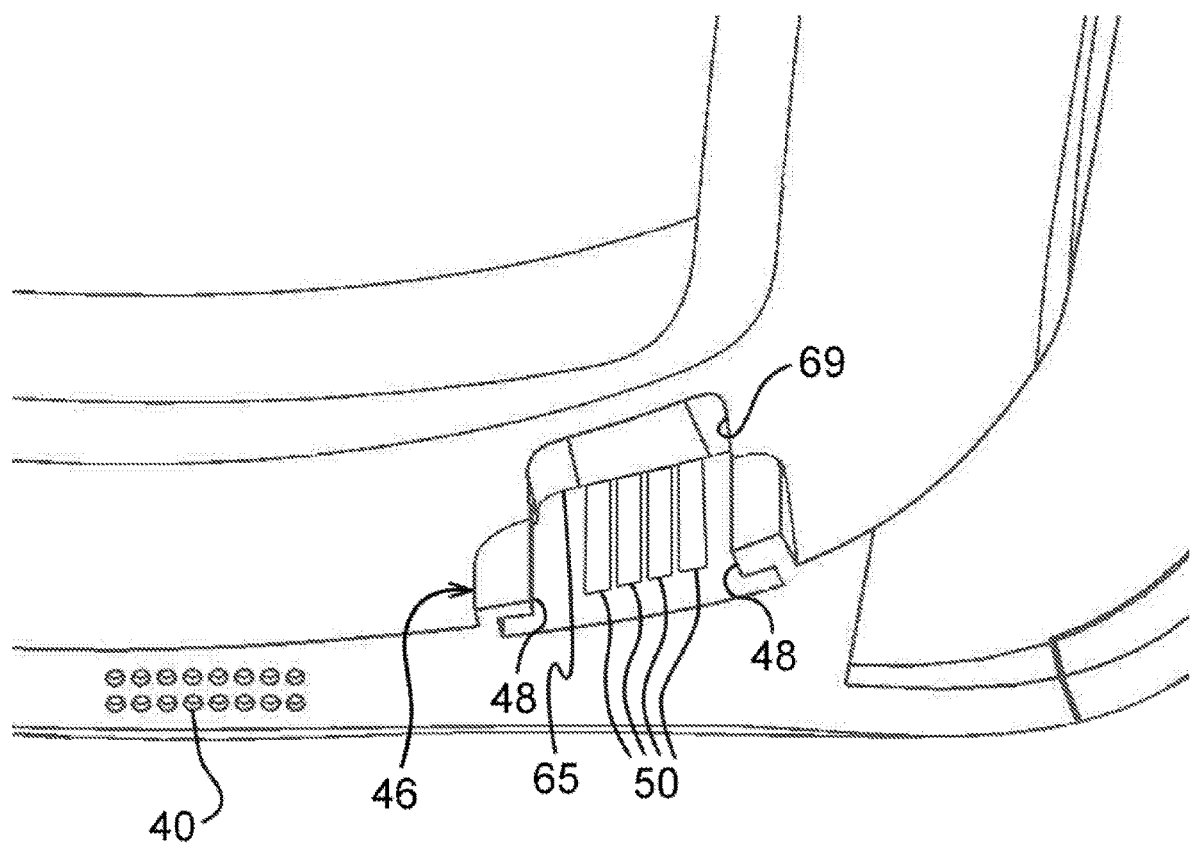
FIG. 5 is an enlarged perspective view, partially cut away of a connection port for a hard hat.

Referring to FIGS. 2 and 3, an adjustable suspension band assembly, generally indicated at 32, extends around an interior 34 (best seen in FIG. 3) of the hard hat 10 to assist in fitting the hard hat 10 to the head securely and comfortably. The adjustable suspension band assembly 32 also absorb energy from impacts and collisions. The adjustable suspension band assembly 32 includes an adjusting device 36 that adjusts the diameter of a primary support loop 38.

Audio ports 40 for audible signals are positioned on the sides of the hard hat 10 at the opening 14. Small speakers (not shown) are housed within the outer shell 12 and produce sound waves that are emitted out the audio ports 40. The connection ports 22 are disposed adjacent the audio ports 40 and allow peripheral devices (none shown) to be secured to the hard hat 10. The connection ports 22 are described in greater detail in United States patent application having Ser. No. 15/087,972, the disclosure of which is expressly incorporated herein by reference.

Also connected to the outer shell 12 near the opening 14 of the hard hat 10 are a set of signaling volume switches 42. The volume switches 42 adjust the volume of the speakers behind the audio ports 40 or any other speakers that may be included in peripheral that may be attached to the hard hat 10.

A signaling light 44 is designed to blink and/or emit light having different wavelengths. The blinking and the wavelength emitted will provide communication to the user of the hard hat 10. The audio ports 40 and the signaling light 44 are considered a subset of the devices set forth above.

The hard hat 10 includes an anchor port 46 formed in the outer shell 12 on the interior 34 thereof. In the embodiment shown in the Figures, there are four anchor ports 46. The anchor port 46 is disposed near the opening 14. The anchor port 46 includes a clip structure 48 (discussed in greater detail subsequently) and an electrical contact 50, which is electrically connected to the control unit 18. As is shown in the Figures, the electrical contact 50 may include a plurality of contacts 50, each having a separate function. For example, one of the plurality of electrical contacts 50 may provide power, a second providing a signal, a third providing a ground. Any combination or number of electrical contacts 50 may be used within the anchor port 46.

The primary support loop 38 of the suspension band assembly 32 includes an electronic peripheral 52. The electronic peripheral 52 is secured, either removably or fixedly, to the primary support loop 38. The electronic peripheral, generally indicated at 52, may include a sensor (not shown) that may sense the body temperature, heart rate, or oxygen level of the user. It should be appreciated by those skilled in the art that the electronic peripheral 52 may include one or more of these sensors and may include other devices and that the list set forth above is not intended to be limiting. The electronic peripheral 52 is covered by a pad 54 to provide comfort and absorb perspiration. The pad 54 includes sensor openings 55 for the sensor(s) and can be removable for washing and/or replacement.

Figure 6:
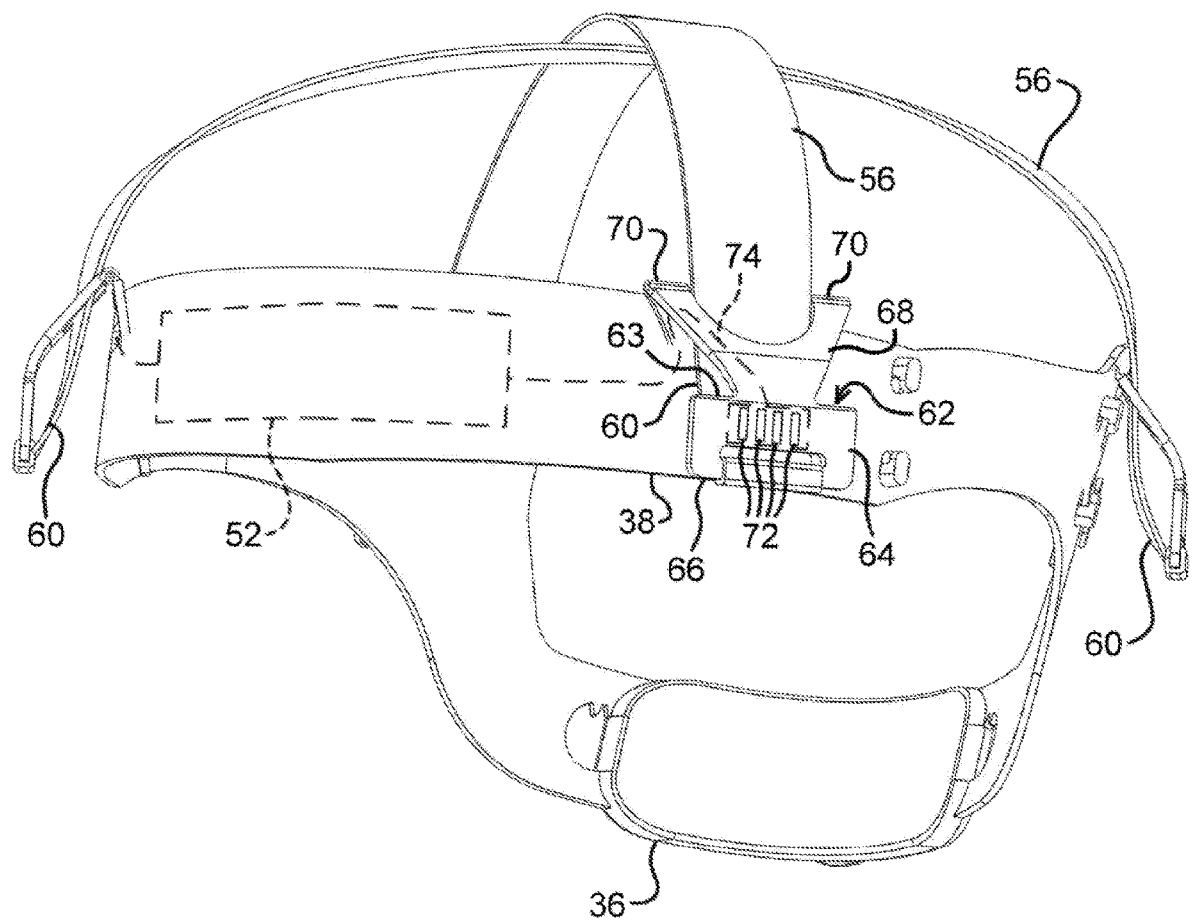
FIG. 6 is a perspective view of the suspension band.
Figure 7:
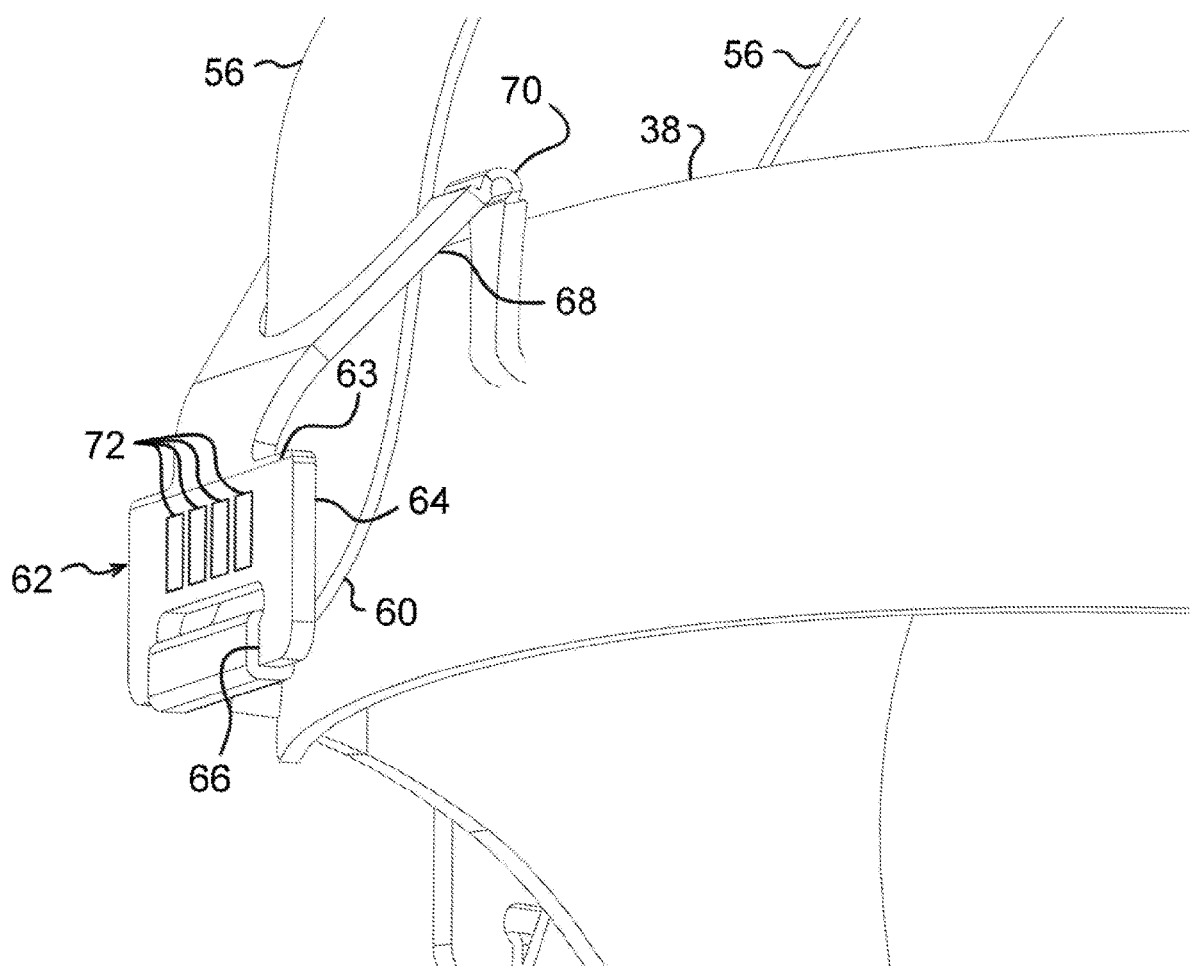
FIG. 7 is an enlarged perspective view, partially cut away, of the suspension band and a connector.
Figure 8:
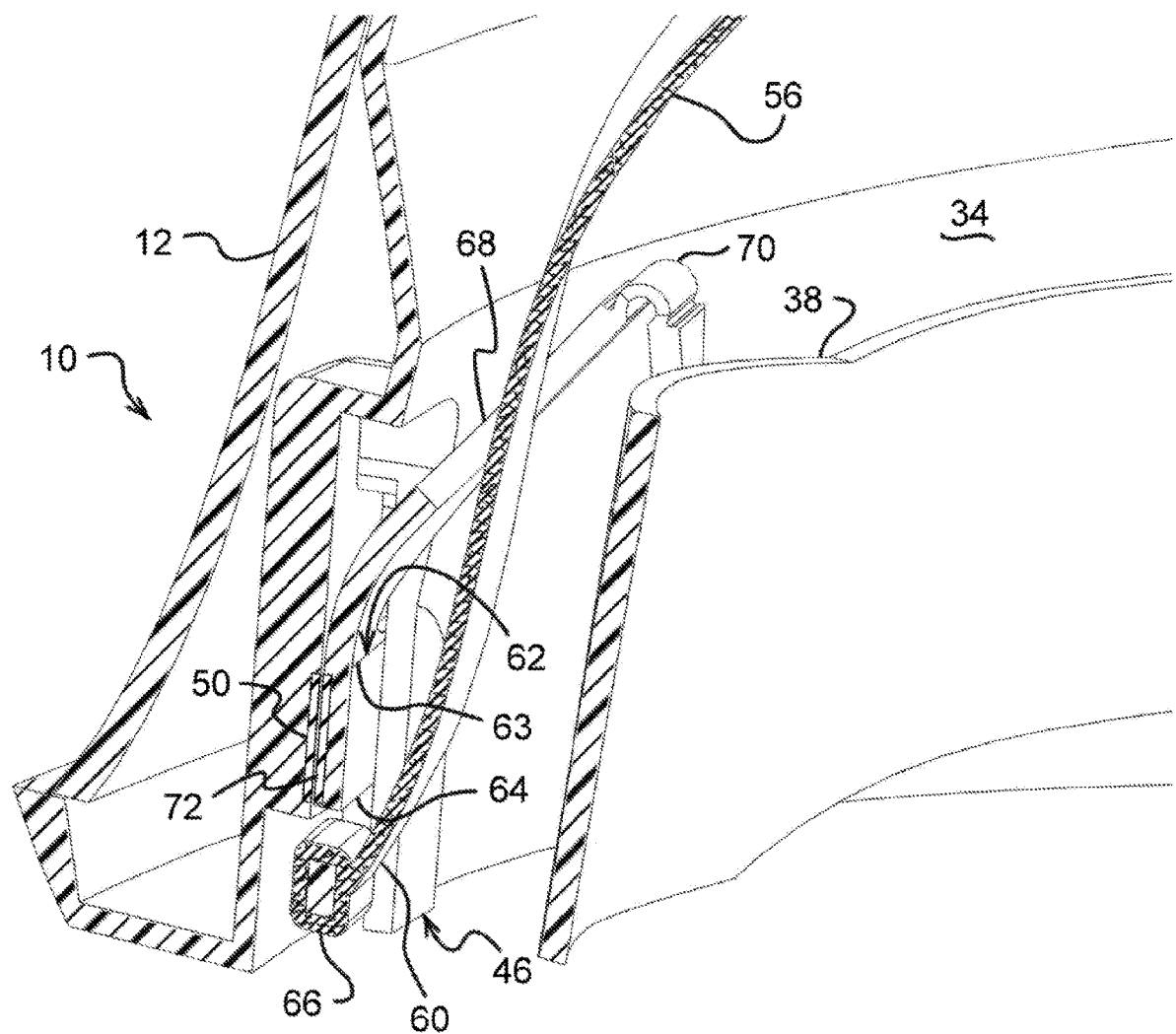
FIG. 8 is a cross-sectional side perspective view of the suspension band taken along lines 8-8 of FIG. 3.

The suspension band assembly 32 includes two attachment straps 56 (see FIG. 6) that extend diametrically over the primary support loop 38 in a manner that provides enough slack to allow the head of the user to comfortably extend through the primary support loop 38. In some instances, the two attachment straps 56 may be adjustable to allow the user to have the two attachment straps 56 rest on the top of his or her head, providing more support and comfort.

Each of the attachment straps 56 define two strap distal ends 60. The strap distal ends 60 are operatively connected to the primary support loop 38. An anchor 62 having an anchor body 64 is fixedly secured to each of the strap distal ends 60. The anchors 62 secure the attachment straps 56 and, hence, the primary support loop 38 to the hard hat 10. The strap distal ends 60 are wrapped around a bar 66, which extends through a portion of the anchor body 64. In other embodiments, the strap distal ends 60 may be fused to the anchors 62. It should be appreciated by those skilled in the art that other options for securing the anchors 62 to the strap distal ends 60 exist.

The anchors 62 are designed to be received by the clip structures 48 of the anchor ports 46. More specifically, the anchors 62 slide into the clip structures 48 from the bottom and are held in place when an anchor top edge 63 abuts an anchor stop 65, which is a surface that extends across the clip structure 48 at the upper end of the anchor ports 46.

The anchors 62 include an anchor body extension 68, which extend up from the anchor top edge 63. The anchor extension 68 extends through a clip 69 in the clip structure 48. The anchor extension 68 is fixedly secured to the primary support loop 38. Therefore, the anchors 62 secure the attachment straps 56 to the primary support loop 38. The anchor extensions 68 extend through a living hinge 70 that provides flexibility in orientation between the anchors 62 and, hence, the outer shell 12, and the primary support loop 38.

An electrical anchor contact 72 is fixedly secured to the anchor 62 and provide an electrical connection between the hard hat 10 and the electronic peripheral 52 on the primary support loop 38. The electrical anchor contact 72 extends along a portion of the anchor body 64. In addition, there may be more than one electrical anchor contact 72. Typically, there would be as many electrical anchor contacts 72 as there are electrical contacts 50 in the anchor ports 46, although this is not necessary.

Extending up from the electrical anchor contact 72 through the anchor extension 68 and through a portion of the primary support loop 38 is an electrical conductor 74. The electrical conductor 74 completes the circuit between the electronic peripheral 52 in the primary support loop 38 and the control unit 18 in or on the outer shell 12 of the hard hat 10.

Figure 9:
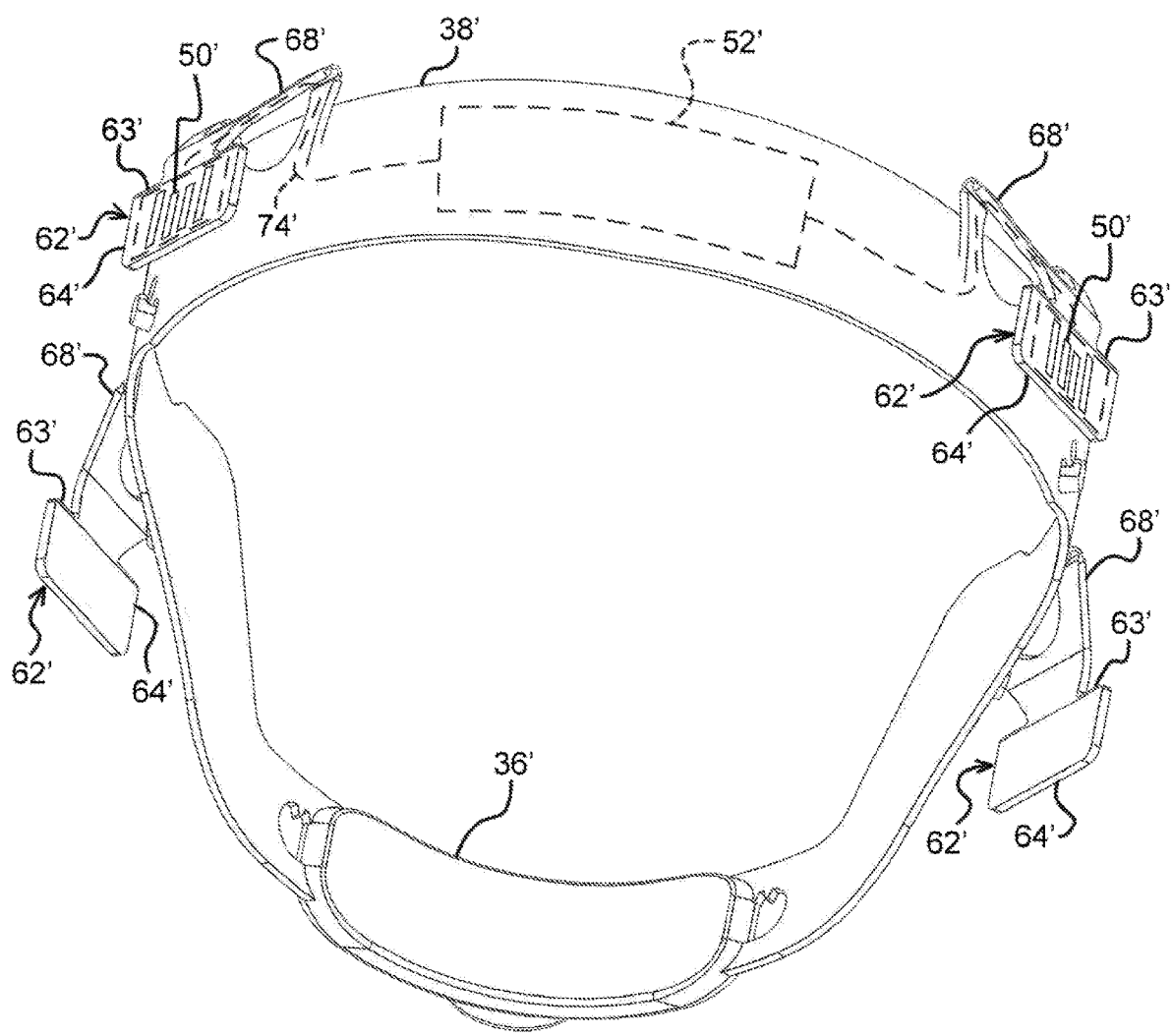
FIG. 9 is a perspective view of an alternative embodiment of the suspension band.

Referring to FIG. 9, wherein like primed reference numerals represent similar elements to those shown in FIGS. 1 through 8, an alternative embodiment of the primary support loop 38' is shown. In this embodiment, the anchors 62' are secured only to the primary support loop 38' using the anchor extension 68'. The attachment straps of the prior embodiment are not used in this embodiment. When this embodiment is used, the hard hat 10 would rest directly on the head of the user.

The invention has been described in an illustrative manner. It is to be understood that the terminology, which has been used, is intended to be in the nature of words of description rather than of limitation.

Many modifications and variations of the invention are possible in light of the above teachings. Therefore, within the scope of the appended claims, the invention may be practiced other than as specifically described.

We claim:

1. A suspension band assembly to be used to support a hard hat on a head of a user, said suspension band assembly comprising:
   a primary support loop to receive the head of the user therein;
   an electronic peripheral secured to said primary support loop;
   at least one attachment strap secured to said primary support loop and extending to a strap distal end;
   an anchor fixedly secured to said strap distal end for securing said primary support loop to the hard hat; and
   an electrical anchor contact fixedly secured to said anchor to provide an electrical connection between the hard hat and said electronic peripheral on said primary support loop.

2. A suspension band assembly as set forth in claim 1 includes a bar around which said distal end of said attachment strap is secured.

3. A suspension band assembly as set forth in claim 1 including an electrical conductor extending between said electrical anchor contact and said electronic peripheral.

4. A suspension band assembly as set forth in claim 3 wherein said anchor includes an extension extending up therefrom to support said electrical conductor.

5. A suspension band assembly as set forth in claim 4 wherein said attachment strap is fixedly secured to said primary support loop with said extension.

6. A suspension band assembly as set forth in claim 5 wherein said extension includes a living hinge.

\* \* \* \* \*